Figure 1:
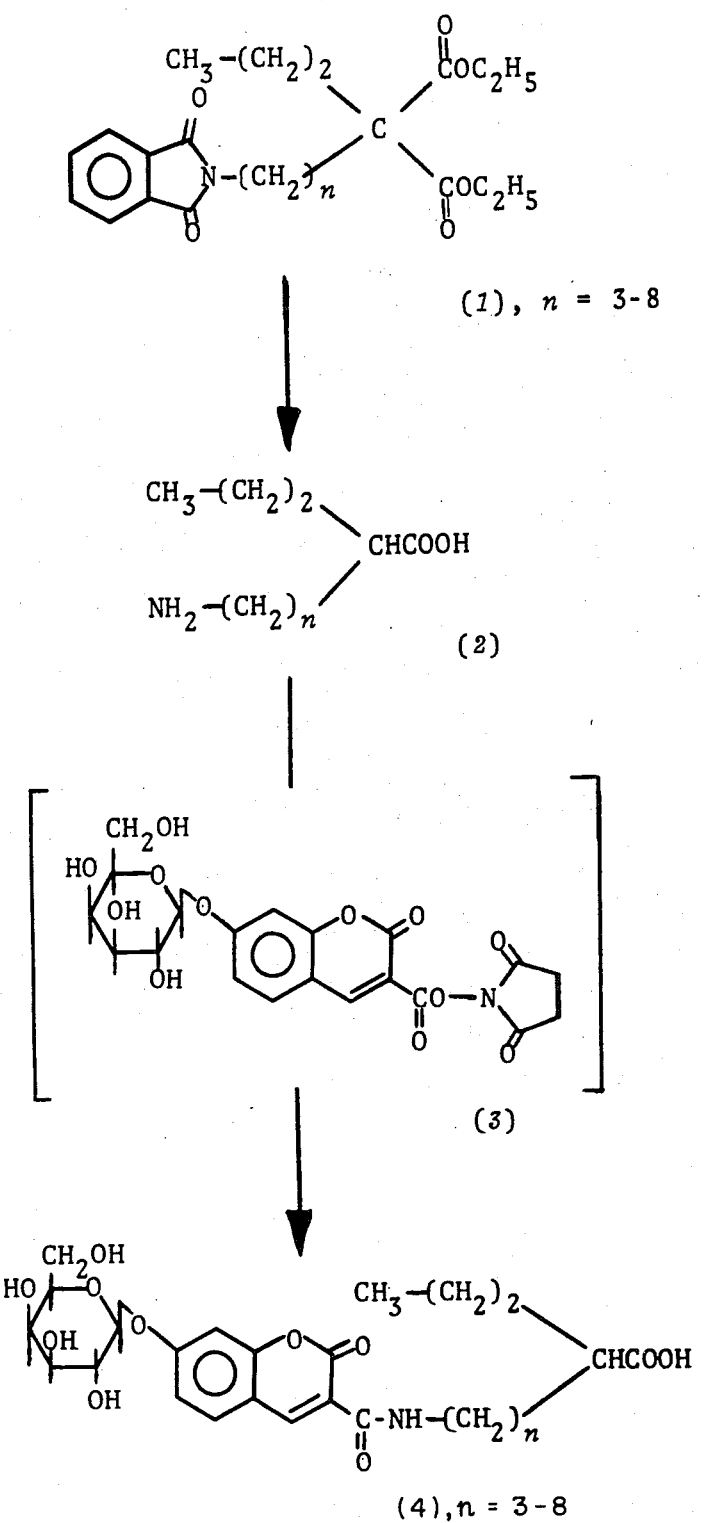

United States Patent [19]

Buckler et al.

[11] 4,292,425

[45] Sep. 29, 1981

[54] β-GALACTOSYL-UMBELLIFERONE VALPROIC ACID CONJUGATES

[75] Inventors: Robert T. Buckler, Edwardsburg, Mich.; John F. Burd; Raphael C. Wong, both of Elkhart, Ind.

[73] Assignee: Miles Laboratories, Inc., Elkhart, Ind.

[21] Appl. No.: 139,716

[22] Filed: Apr. 14, 1980

Related U.S. Application Data

[62] Division of Ser. No. 93,372, Nov. 13, 1979.

[51] Int. Cl.³ .................... C07H 15/22; C07H 17/04
[52] U.S. Cl. ......................................... 536/4; 424/180
[58] Field of Search ............................. 536/4; 424/180

[56]  References Cited

U.S. PATENT DOCUMENTS 4,226,978  10/1980  Boguslaski et al. .................... 536/4
4,238,389  12/1980  Leung et al. ........................... 536/4

OTHER PUBLICATIONS

Chemical Abstract, vol. 87, 1977, p. 4, Abst. No. 161337b, Burd et al., "Homogenous Reactant–Labelled Fluorescent Immunoassay for Therapeutic Drugs."

*Primary Examiner*—Delbert R. Phillips
*Assistant Examiner*—Blondel Hazel
*Attorney, Agent, or Firm*—Andrew L. Klawitter

[57]  ABSTRACT

Reagents for use in binding assays, particularly immunoassays, to determine valproic acid in liquid media such as serum. Such reagents include antibody to valproic acid and β-galactosyl-umbelliferone-valproic acid conjugates. Also provided are compounds used to prepare such reagents, including valproic acid immunogen conjugates and intermediates in the synthesis of such immunogen conjugates and β-galactosyl-umbelliferone-labeled conjugates.

2 Claims, 2 Drawing Figures

βGALACTOSYL-UMBELLIFERONE VALPROIC ACID CONJUGATES

This is a division, of application Ser. No. 93,372, filed Nov. 13, 1979.

BACKGROUND OF THE INVENTION

1. Field of the Invention

This invention relates to novel valproic acid derivatives pertaining to binding assays, especially immunoassays, for determining valproic acid and its salt forms in liquid media such as serum. Such derivatives include labeled valproic acid conjugates directly used in performing such assays. Also provided are antibodies to valproic acid and immunogen conjugates useful in stimulating production of such antibodies in host animals according to conventional techniques. Further provided are intermediates in the synthesis of the aforementioned labeled conjugates and immunogen conjugates.

Valproic acid (2-n-propylpentanoic acid) and its various salt forms, particularly its sodium salt, are anticonvulsant drugs useful in the management of epilepsy. The structural formula for the acid is as follows:

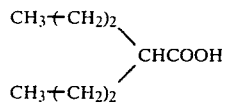

cf. *The Merck Index*, 9th ed., No. 9574(1976).

Due to its rapid elimination, blood levels of valproic acid fluctuate considerably. There is only a poor correlation between daily dose and blood concentration, possibly due to interindividual differences in absorption or total body clearance. Therefore, the proper management of epilepsy with the drug cannot be achieved by the simple choice of a medication regimen based on body weight, surface area, or age of the patient. Frequent administration and determination of individual blood concentrations at accurately fixed times appear to be the only reliable monitoring method. No clear therapeutic blood levels have been firmly established. However, some physicians accept 50 to 100 μg/ml of valproic acid as the range of therapeutic blood level since most patients with blood levels in this range seem adequately controlled [Pinder et al, *Drug* 13:94(1977)].

2. Description of the Prior Art

At present valproic acid is usually analyzed by gas-liquid chromatography [Libeer et al, *J. Chromatogr.* 160:285(1978)], with high-pressure liquid chromatography also being used [Sutheimer et al, *Chromatogr. Newsletter* 7:1(1979)]. There is presently no commercially available immunoassay for valproic acid. An abstract has been published regarding a homogeneous enzyme immunoassay for valproic acid [*Clin. Chem.* 25:1093(1979)]. No details were given concerning any of the reagents which might be used in such an assay.

Nonradioisotopic specific binding assays employing an enzyme-cleavable substrate label are described in German Offenlegungschriften Nos. 2,618,419 and 2,618,511, corresponding respectively to U.S. patent applications Ser. Nos. 667,982 and 667,996, both filed Mar. 18, 1976, and assigned to the present assignee. The assays avoid the use of radioisotopic labels and can be performed in homogeneous or heterogeneous formats. In the heterogeneous format, the bound- and free-species of the labeled conjugate are physically separated and the label measured in one of the separated species, whereas in the homogeneous format, the label expresses a different activity in the bound-species compared to the free-species, permitting performance of the assay without a separation step. In the aforementioned assays, the labeled conjugate serves as a substrate for a cleaving enzyme, with cleavage of the conjugate producing a distinguishable indicator product, usually a fluorescent product. The fluorescers umbelliferone or fluorescein are coupled to the ligand under assay through an ester bond which upon cleavage by an esterase releases the free fluorescent products, umbelliferone and fluorescein, respectively.

An improved substrate-labeled specific binding assay is described in pending U.S. patent application Ser. No. 886,094, filed Mar. 13, 1978, and the continuation-in-part application (Docket No. 11910) based thereon filed on or about Oct. 19, 1979, both assigned to the present assignee, and by Burd et al, *Clin. Chem.* 23:1402(1977). The improvement comprises employing as the label component of the labeled conjugate, a residue of the formula "G-D-R" wherein G is a glycone, D is a dye indicator moiety, and R is a linking group through which the dye indicator moiety is covalently bound to the binding component (usually the ligand under assay or a binding analog thereof) of the labeled conjugate. The cleaving enzyme employed is a glycosidase which cleaves the bond between the glycone and the dye indicator moiety, releasing a detectable, usually fluorescent, fragment comprising the dye indicator moiety coupled to said binding component (e.g., the ligand). Most preferably, the glycone is a β-galactosyl group and the dye indicator moiety is umbelliferone.

SUMMARY OF THE INVENTION

The present invention provides β-galactosyl-umbelliferonevalproic acid conjugates of the formula:

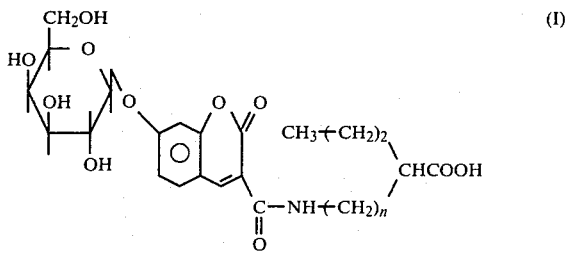

wherein n is an integer from 3 through 8, and preferably is 4. As illustrated in FIG. 1 of the drawing and as described in more detail in the examples below, the labeled conjugates (I) are generally prepared by reaction of carboxyl-activated 7-β-galactosylcoumarin-3-carboxylic acid with appropriate ω-amino-2-n-propylalkanoic acids of the formula:

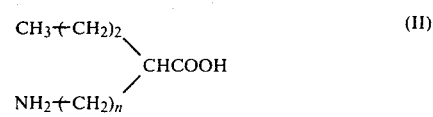

wherein n is the same as described above. The reaction proceeds in an aqueous, neutral pH, solvent at between 0° and 25° C. for between 1 and 3 hours. The ω-amino-2-n-propylalkanoic acids (II) are prepared according to the malonic ester synthesis of carboxylic acids [*Prepara-* tive *Organic Chemistry*, ed. Hilgetag and Martini, John Wiley & Sons (New York 1972), p. 912].

It is evident that numerous functional equivalents of the labeled conjugates (I) can be prepared by one with ordinary skill in the art without departing from the inventive features hereof. For example, the umbelliferyl residue can be substituted, particularly at its 4, 5, 6 or 8 positions with appropriate groups while not substantially altering the ability of the modified labeled conjugate to act as a substrate for $\beta$-galactosidase or to be bound by a binding partner, e.g., antibody, to the valproic acid analogue moiety. Such equivalents will have the same function as labeled conjugates (I) and can be prepared by appropriate selection of starting materials or appropriate chemical modification after formation of such labeled conjugates. Representative of the types of substituents that can be incorporated into the umbelliferyl residue to form equivalent compounds include, without limitation, lower alkyl, e.g., methyl, ethyl and butyl; halo, e.g., chloro and bromo; nitro; carboxyl; carbo lower alkoxy, e.g., carbomethoxy and carbethoxy; amino; mono- and di-lower alkylamino, e.g., methylamino, dimethylamino and methylethylamino; amide; hydroxyl; lower alkoxy, e.g., methoxy and ethoxy; and so forth.

Figure 2:
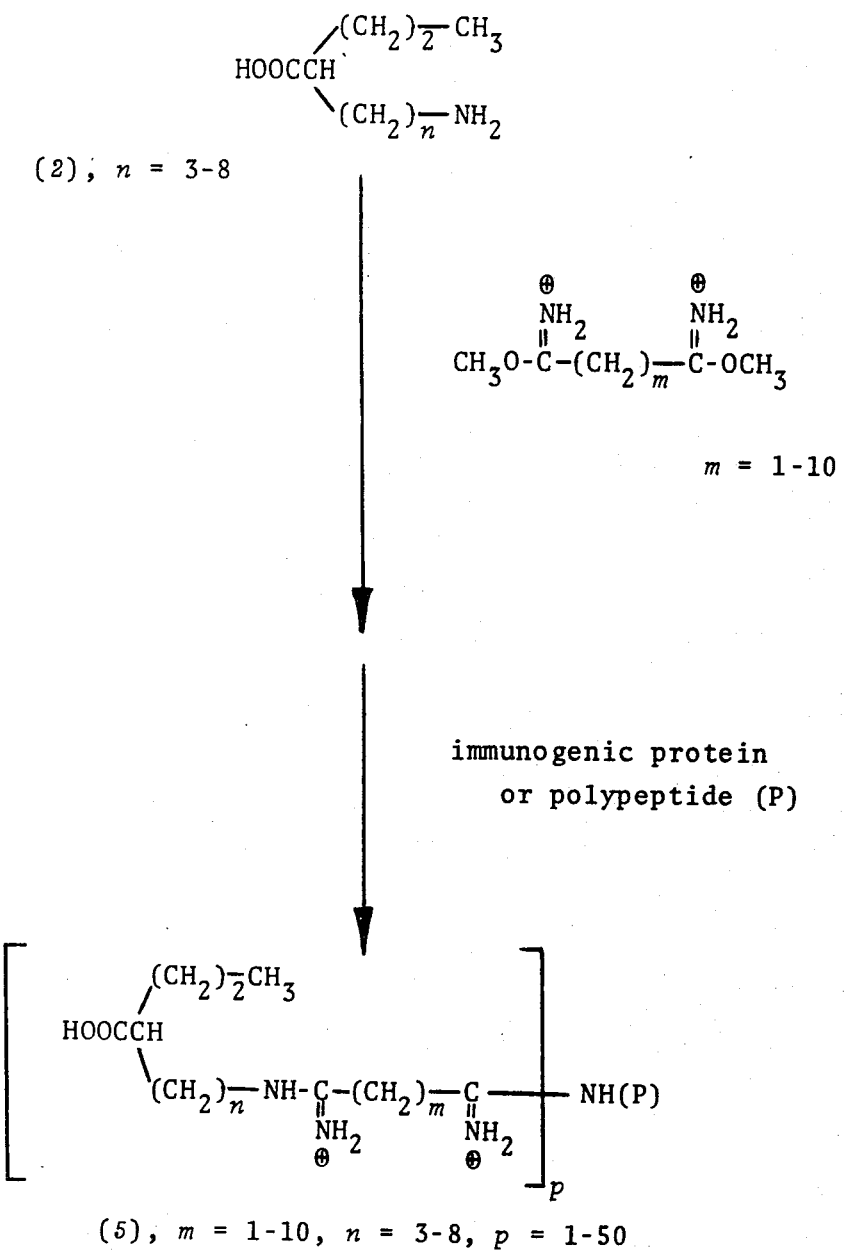

Also provided are antibodies to valproic acid prepared by conventional techniques against immunogen conjugates of the formula:

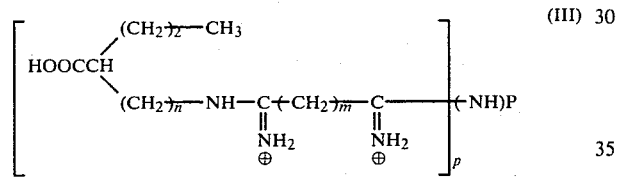
(III)

wherein —(NH)P is a conventional immunogenic protein or polypeptide (sometimes referred to as an immunogenic carrier) bound through an amino group thereof, n is the same as defined above, m is an integer from 1 through 10, preferably 4, and p is on the average from 1 to the number of available amino groups in P. As illustrated in FIG. 2 of the drawing and as described in more detail in the examples below, the immunogen conjugates (III) are prepared by coupling an appropriate amino-functionalized alkanoic acid (II) to the desired immunogenic protein or polypeptide with a bifunctional bis-imidate of the general formula:

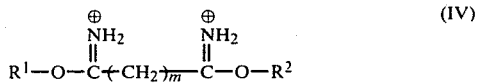
(IV)

wherein m is as defined above and $R^1$ and $R^2$, which may be the same or different but which more usually are the same, are alkyl, preferably lower alkyl (i.e., having 1-4 carbon atoms) such as methyl, ethyl, n-propyl, isopropyl, and so forth. Particularly preferred bis-imidates (IV) are the dimethyl alkyl-bis-imidates, especially dimethyl adipimidate. The bis-imidates are generally available from commercial sources or may be prepared by published methods by those having ordinary skill in the art [Hunter and Ludwig, *J. Am. Chem. Soc.* 84:3491(1972)]. The bis-imidates will normally be provided in a suitable salt form which upon dissolution in the aqueous reaction media generates the positively charged bis-imidate species (IV). Correspondingly, iso-lation of the labeled conjugate (I) from aqueous media such as by solvent evaporation or precipitation yields salt forms wherein the counter anions to the protonated imino groups are taken from available anions in the media.

The use of bis-imidates in the coupling of proteins and polypeptides is described in the literature, for example, *Affinity Chromatography*, Lowe and Dean, John Wiley and Sons (New York 1974), p. 238; *Methods in Enzymology and Immunochemistry*, ed. Williams and Chase, Academic Press (New York), pp. 320–322; and *Proc. Nat. Acad. Sci. USA* 66:651–656(1970). As applied in the present invention, the coupling reaction is allowed to proceed in aqueous solution under mild conditions, e.g., at a pH between about 7 and about 10, more usually between 8 and 9, and at temperatures between about 0° C. and about 40° C., more usually between 20° C. and 30° C. Usually, the amino-functionalized alkanoic acid (II), the bis-imidate (IV), and the desired immunogenic protein or polypeptide are added in sequence, with a short incubation period for reaction between the amino-functionalized alkanoic acid and the bis-imidate of between 1 and 30 minutes, followed by addition of the protein or polypeptide and a second incubation period lasting between 10 minutes and 4 hours.

It has been generally found that the longer the second incubation period, the greater the degree of substitution of the valproic acid analogue moiety on the protein or polypeptide, i.e., the higher the value of p in formula (III), or expressed another way, the greater the epitopic density on the immunogenic carrier. The upper limit on the number of valproic acid analogue moieties that can be introduced to a given protein or polypeptide is theoretically limited only be the number of available amino groups in such protein or polypeptide. By available amino groups is meant those amino groups which are reactive with the bis-imidate coupling agent. Under the current state of knowledge, such amino groups comprise (a) the terminal $\alpha$-amino groups of the peptide chain in the protein or polypeptide and (b) the $\epsilon$-amino groups of lysyl residues occurring in the protein or polypeptide. The degree of substitution (i.e., the value of p) of the valproic acid analogue moiety will vary between 1 and such theoretical upper limit depending on the characteristics desired for the antibody to be prepared therefrom. Normally, p will be on the average between 1 and 50, more usually between 1 and 25.

The immunogenic protein or polypeptide used may be selected from any of those conventionally known. For the most part, such proteins and polypeptides will have a molecular weight between 5,000 and 1,000,000, preferably between 15,000 and 500,000, and more usually between 30,000 and 200,000. Generally, proteins taken from one species will be immunogenic when introduced to the blood stream of another species. Particularly useful proteins are albumins, globulins, enzymes, hemocyanins, albuminoids, glutelins, proteins having sigificant nonproteinaceous constituents, e.g., glycoproteins, and the like. The albumins and globulins of molecular weight between 30,000 and 200,000 are particularly preferred.

Preparation of specific antibodies using the present immunogen conjugates may follow any conventional technique. Numerous texts are available describing the fundamental aspects of inducing antibody formation, for example reference may be made to Parker, *Radioimmunoassay of Biologically Active Compounds*, Prentice- Hall (Englewood Cliffs, N.J. USA, 1976). In the usual case, a host animal such as a rabbit or goat is injected at one or more of a variety of sites with the immunogen conjugate, normally in mixture with an adjuvant. Further injections are made at the same or different site or sites at regular or irregular intervals thereafter with bleedings being taken to assess antibody titer and its rate of increase until it is determined that optimal titer has been reached. The host animal is bled to yield a suitable volume of specific antiserum. Where desirable, purification steps may be taken to remove undesired material such as non-specific antibodies before the antiserum is considered suitable for use in performing actual assays.

The present invention will now be illustrated, but is not intended to be limited, by the following examples.

PREPARATION OF β-GALACTOSYL-UMBELLIFERONE-LABELED VALPROIC ACID CONJUGATES

The conjugates are prepared according to the reaction scheme shown in FIG. 1 of the drawing. This synthetic route is exemplified by the following method of preparing N-(5-carboxyoctyl)-7-β-galactosylcoumarin-3-carboxamide (4), n=4.

6-Amino-2-n-propylhexanoic Acid (2), n=4.

To a stirred suspension of 6.24 grams (g) (0.13 mol) of sodium hydride (50% mineral oil dispersion) in 100 milliliters (ml) of dry dimethylformamide was slowly added 25.3 g (0.13 mol) of diethyl n-propylmalonate (Pfaltz & Bauer, Inc., Stamford, Connecticut USA). After one hour, hydrogen evolution ceased. To this was slowly added a solution of 36.7 g (0.13 mol) of N-(4-bromobutyl)phthalimide (Aldrich Chemical Co., Milwaukee, Wis. USA) in 50 ml of dry dimethylformamide. The reaction was stirred at room temperature for 3 hours, then heated at 60° C. for 12 hours. It was cooled, quenched with 25 ml of 1:1 (volume:volume) (v:v) acetic acid:water, and the solvent removed under reduced pressure. The residue was partitioned between ethyl acetate and water. The organic phase was separated, dried, and evaporated to give 54.8 g of the crude diester (1), n=4. This was not characterized but instead was heated for 20 hours in 500 ml of dry ethanol containing 73 g (0.65 mol) of potassium tert-butoxide. After this, 150 ml of water was added and heating continued for an additional 3 hours. The reaction was cooled and most of the ethanol removed under reduced pressure. The concentrate was diluted with water, washed with ether, and acidified with hydrochloric acid. It was extracted with three 250 ml portions of ethyl acetate. The extracts were combined, dried, and evaporated to give a solid residue. Hydrolysis was completed by refluxing this residue in 500 ml of 1:1 (v:v) dioxane:20% hydrochloric acid.

Evaporation of the dioxane-acid solution gave a residue that was chromatographed on 500 g of silica gel eluting with a solvent prepared by equilibrating equal volumes of chloroform, methanol, and concentrated aqueous ammonium hydroxide solution and discarding the upper phase. Fractions of 20 ml volume were collected. Fractions 122 to 149 were pooled, evaporated, and the residue recrystallized from ethanol to give 4 g (18% yield) of 6-amino-2-n-propylhexanoic acid (2), n=4, as white crystals, mp (melting point) 209°–210° C.

Analysis: Calculated for $C_9H_{19}NO_2$: C, 62.39; H, 11.05; N, 8.09. Found: C, 62.12; H, 11.12; N, 8.27. Infrared Spectrum (KCl): 1635 cm$^{-1}$ (carbonyl).

N-(5-Carboxyoctyl)-7-β-galactosylcoumarin-3-carboxamide (4), n=4

A mixture of 24 g of potassium hydroxide, 80 ml of water, and 240 ml of methanol was stirred at 5° C. while 20 g (0.035 mol) of ethyl 7-β-galactosylcoumarin-3-carboxylate [Burd et al, Clin. Chem. 23:1402(1977)] was added in one portion. After 5 minutes the reaction was heated for 15 hours at 50° C. When cool, the methanol was removed under reduced pressure and the remaining aqueous solution acidified to pH 2 with concentrated hydrochloric acid. The white precipitate was collected, washed with cold water, and recrystallized from hot water. The crystals were washed with acetone and dried at 80° C. for 1 hour. This gave 12 g of 7-β-galactosylcoumarin-3-carboxylic acid as white crystals, mp 250°–255° C.

Analysis: Calculated for $C_{16}H_{16}O_{10}$: C, 52.17; H, 4.38. Found: C, 52.31; H, 4.63.

A solution of 734 milligrams (mg) [2 millimol (mmol)] of 7-β-galactosylcoumarin-3-carboxylic acid and 210 mg (2 mmol) of N-hydroxysuccinimide in 20 ml of dimethylformamide was cooled to −10° C. while stirring under an inert atmosphere. To this was added 412 mg (2 mmol) of dicyclohexyl carbodiimide. After 15 minutes at −10° C., a clear solution was obtained. The reaction was allowed to warm to room temperature and stirred for 2 hours. It was again cooled to −10° C. and the precipitate of dicyclohexyl urea removed by filtration under vacuum. The filtrate, now containing the activated ester (3), was placed in a dropping funnel and added dropwise over a 15 minute period to a 0° C. solution consisting of 346 mg (2 mmol) of 6-amino-2-n-propylhexanoic acid (2), n=4, and 0.5 ml of triethylamine in 20 ml of water. After 1 hour at 0° C., the reaction was allowed to warm to room temperature and stirred for 2 hours. Ten grams of silicic acid was added and the solvent removed on the rotary evaporator under high vacuum. The impregnated silicic acid was placed atop a column of 120 g of silicic acid packed in 3:2 (v:v) ethyl acetate:ethanol. The column was eluted with this solvent and 15 ml fractions were collected. Fractions 28 to 40 were combined, evaporated, and the residue recrystallized from ethanol to give 365 mg (35% yield) of the labeled conjugate (4), n=4, as cream colored crystals, mp 162° C.

Analysis: Calculated for $C_{25}H_{33}NO_{11}$: C, 57.35; H, 6.35; N, 2.68. Found: C, 57.07; H, 6.45; N, 2.65. Infrared Spectrum (KCl): 1710 cm$^{-1}$ (carbonyl).

The above-described synthesis of the labeled conjugate (4), n=4, can be modified to yield β-galactosyl-umbelliferone-labeled valproic acid conjugates wherein n=3–8 by replacing the starting material N-(4-bromobutyl)phthalimide in the described synthesis with the appropriate N-(ω-bromoalkyl) phthalimide as follows:

| n | N-(ω-bromoalkyl)phthalimide |
| --- | --- |
| 3 | N-(3-bromopropyl)phthalimide |
| 5 | N-(5-bromopentyl)phthalimide |
| 6 | N-(6-bromhexyl)phthalimide |
| 7 | N-(7-bromoheptyl)phthalimide |
| 8 | N-(8-bromooctyl)phthalimide |

PREPARATION OF VALPROIC ACID IMMUNOGEN CONJUGATES

The immunogen conjugates are prepared according to the reaction scheme shown in FIG. 2 of the drawing. This synthetic route is exemplified below for preparing immunogen conjugate (5) wherein m and n=4, p is on the average approximately 16, and P represents bovine serum albumin (BSA).

12.9 mg [75 micromol ($\mu$mol)] of 6-amino-2-n-propyl-hexanoic acid (2), n=4, was dissolved in 0.5 ml anhydrous methanol and 36.8 mg (150 $\mu$mol) of dimethyl adipimidate dihydrochloride, along with 24 microliters ($\mu$l) (172.5 $\mu$mol) of triethylamine were added. The solution was allowed to react for 15 minutes at room temperature before adding it to the protein solution which was prepared by dissolving 125 mg (2.08 $\mu$mol) of bovine serum albumin in 2.5 ml of 0.1 molar (M) sodium phosphate buffer, pH 8.5. The reaction solution was mixed and allowed to react for 2 hours. The reaction was stopped by adding 2.5 ml of 1 millimolar (mM) glycine and chromatographed with 0.85% sodium chloride solution through a 3×53 cm column of G-25 Sephadex gel (Pharmacia, Piscataway, New Jersey USA). The ultraviolet absorbance of the 6 ml fractions was monitored and the immunogen conjugate eluting in the column void volume (fractions 21 to 24) was pooled. The unreacted valproic acid derivative eluted in fractions 45 to 56.

Applying the method of Satake et al, *J. Biochem* (Tokyo) 47:654(1960), the average number of free amino groups per molecule of BSA before and after conjugation was determined to be 66 and 50, respectively. The difference, 16, approximates the average number of valproic acid analogue moieties per BSA molecule.

The above-described synthesis of the immunogen conjugate (5), m and n=4, can be modified to yield immunogen conjugates wherein m=1-10 and n=3-8 by replacing, respectively, dimethyl adipimidate with the appropriate dimethyl alkyl-bis-imidate as indicated below, and 6-amino-2-n-propylhexanoic acid with the appropriate $\omega$-amino-2-n-propylalkanoic acid (2) prepared as described hereinabove.

| m | dimethyl alkyl-bis-imidate |
|---|---|
| 1 | dimethyl malonimidate |
| 2 | dimethyl succinimidate |
| 3 | dimethyl glutarimidate |
| 5 | dimethyl pimelimidate |
| 6 | dimethyl octane-bis-imidate |
| 7 | dimethyl nonane-bis-imidate |
| 8 | dimethyl decane-bis-imidate |
| 9 | dimethyl undecane-bis-imidate |
| 10 | dimethyl dodecane-bis-imidate |

BINDING ASSAY FOR VALPROIC ACID

A. Assay Reagents

1. Antiserum—Collected from rabbits which had been immunized with the immunogen conjugate prepared as described above.
2. Buffer—Bicine buffer [N,N-bis-(2-hydroxyethyl) glycine, Calbiochem, La Jolla, California USA] at 50 mM, pH 8.5, at 25° C.
3. Enzyme—*E. Coli* grade IV $\beta$-galactosidase from Worthington Biochemicals Co., Freehold, New Jersey USA. One unit of enzyme hydrolyzes 1.0 $\mu$mole of o-nitrophenyl-$\beta$-D-galactoside per minute at 25° C. in 50 mM Bicine Buffer, pH 8.5, containing 3 mM o-nitrophenyl-$\beta$-D-galactoside.
4. Valproic acid standards—Prepared from liquid valproic acid obtained from Abbott Laboratories, North Chicago, Ill. USA.
5. Fluorogenic Valproic Acid Reagent—Solution of 0.016 absorbance units at 343 nanometers (nm) of $\beta$-galactosyl-umbelliferone-labeled valproic acid conjugate prepared as described above in 5 mM formate - 0.1% azide buffer, pH 3.5, containing 0.1% Tween 20 (polyethylene sorbitan monolaurate from J. T. Baker, Pillipsburg, New Jersey USA).

B. Apparatus

Fluorescence was measured with an Aminco Fluorocolorimeter (American Instruments Co., Silver Springs, Maryland USA). Excitation and emission wavelengths were set at 400 and 450 nm, respectively. All fluorescence measurements were conducted at 25° C.

C. Assay Procedure

A reagent was prepared in the buffer to contain 0.5 units of the enzyme per ml and an amount of antiserum sufficient to decrease the enzyme reaction to about 45% of that observed in the absence of antiserum. To 3.0 ml of this reagent in individual cuvettes was added 100 $\mu$l of valproic acid standards which had previously been diluted 1 part to 50 parts of buffer. At 30 second intervals 100 $\mu$l of the Fluorogenic Valproic Acid Reagent was added to the cuvettes and the contents mixed by gentle inversion of the cuvettes. At 20 minutes after addition of the Fluorogenic Valproic Acid Reagent, the fluorescence intensity in the individual cuvettes were measured. The results are given in the following table.

| Valproic Acid Concentration in the Serum Standard ($\mu$g/ml) | Fluorescence Intensity (Arbitrary units) |
|---|---|
| 250 | 77 |
| 150 | 66 |
| 100 | 57 |
| 50 | 39 |
| 0 | 6 |

Thus, it was demonstrated that the reagents of the present invention are useful in a binding assay for determining valproic acid in liquid media.

What is claimed is:

1. A $\beta$-galactosyl-umbelliferone-valproic acid conjugate of the formula:

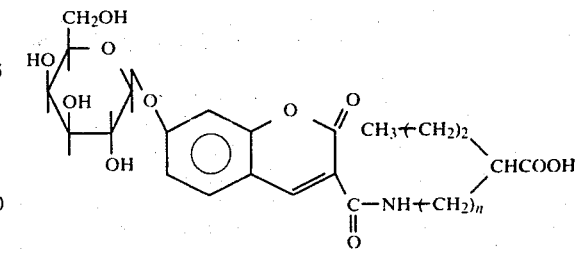

wherein n is an integer from 3 through 8.

2. The conjugate of claim 1 wherein n=4.

* * * * *